United States Patent [19]

Zhu et al.

[11] Patent Number: 5,110,434
[45] Date of Patent: May 5, 1992

[54] USE OF ZWITTERIONS TO MOBILIZE ISOELECTRICALLY FOCUSED AMPHOLYTE ZONES

[75] Inventors: Minge-De Zhu, Berkeley; Roberto Rodriguez, Richmond; C. Timothy Wehr, Albany, all of Calif.

[73] Assignee: Bio-Rad Laboratories, Inc., Hercules, Calif.

[21] Appl. No.: 633,646

[22] Filed: Dec. 20, 1990

[51] Int. Cl.$^5$ .................... C25B 1/00; B01D 57/02
[52] U.S. Cl. ............................ 204/183.2; 204/180.1
[58] Field of Search ............... 204/182.9, 183.2, 183.3

[56] References Cited

U.S. PATENT DOCUMENTS 4,725,343 2/1988 Hjerten et al. .................. 204/183.2
4,911,808 3/1990 Hjerten ........................... 204/182.9

OTHER PUBLICATIONS

S. Hjerten et al., *J. Chromatog.* 346:265–270 (1985).
S. Hjerten et al., *J. Chromatog.* 387:127–138 (1987).
S. Hjerten et al., *J. Chromatog.* 347:191–198 (1985).

*Primary Examiner*—John Niebling
*Assistant Examiner*—Caroline Koestner
*Attorney, Agent, or Firm*—Townsend and Townsend

[57] ABSTRACT

Ampholytic solute zones which have been stabilized by isoelectrical focusing in a separation medium such as a capillary are mobilized by the introduction of a relatively large quantity of zwitterion to one of the electrode chambers. When a voltage is then applied between the electrode chambers as in the focusing stage, the zwitterion migrates into the separation medium in accordance with the isoelectric point of the zwitterion. The voltage is maintained to caused continuous migration of the zwitterion into the capillary, thereby forming an expanding zone which displaces the focused zones formed in the focusing stage and causes them to travel axially through the capillary toward a detection point or out of the capillary for purposes of recovery.

11 Claims, 1 Drawing Sheet

USE OF ZWITTERIONS TO MOBILIZE ISOELECTRICALLY FOCUSED AMPHOLYTE ZONES

This invention lies in the field of isoelectric focusing, and relates in particular to methods for mobilizing a focused pattern of ampholytes, such as proteins for example, in a focusing medium for purposes of recovery, detection or both.

BACKGROUND OF THE INVENTION

Capillary electrophoresis is a technique of considerable interest in the analysis of biological mixtures, particularly mixtures of small peptides, proteins and nucleic acids, since it can be used on extremely small samples and permits the use of high voltages which produce separations at high speed. Capillaries also offer the advantage of permitting on-line (i.e., on-tube) detection, a simple and highly efficient means of detection which avoids the need for time-consuming steps such as staining and derivatization of the solutes, and avoids dilution of the solutes and the risk of inaccuracies due to peak broadening or mixing upon emergence of the solutes from the capillary. A particularly useful form of capillary electrophoresis for certain types of biological mixtures, particularly proteins, is isoelectric focusing, which separates solutes on the basis of their isoelectric points.

On-tube detection is an important advantage of capillary electrophoresis since it allows monitoring the separated components while the experiment is in progress without loss in resolution and without the need for staining or derivatizing separated components. However, in capillary isoelectric focusing the components remain focused in stationary zones at the completion of the separation process. Detection of the separated components can be achieved either by scanning the length of the capillary or by mobilizing the focused zones past a single detection point in the capillary (i.e., on-tube detection) or to an external detector. Mobilization techniques are preferred over scanning since they avoid the need for motorized scanning equipment and provide higher sensitivity. Mobilization also permits recovery of isolated zones individually for preparative purposes as they emerge from the capillary.

Mobilization has been achieved in a variety of ways. One method is by hydrodynamic flow, which involves pumping a solution through the capillary to displace the separation medium past the detection point or out of the capillary, depending on which type of detection technique is used and whether or not solute recovery is sought. A problem encountered in this technique is parabolic zone distortion. In certain systems, this can be suppressed by the use of a sucrose gradient in the focusing stage. Unfortunately, such systems are limited to those with a relatively large diameter column, i.e., 3–20mm for example, rather than a capillary, and only when such columns are mounted in a vertical position. A further disadvantage is that hydrodynamic flow mobilization is not possible when the focusing medium is a gel.

An alternative mobilization technique is disclosed by Hjertén, et al., U.S. Pat. No. 4,725,343, issued Feb. 16, 1988. Mobilization according to this technique is achieved by first changing the pH of either the anolyte or the catholyte after focusing, to place the pH's of the anolyte and catholyte either both above or both below the entire range of isoelectric points of the focused ampholyte zones. When a voltage is then applied between the anolyte and catholyte, the entire ampholyte zone pattern moves as a unit through the separation medium. The preferred embodiment in the patent is the replacement of the anolyte used in the focusing step with the same solution used for the catholyte, or vice versa, with the result that the two ends of the separation medium are in electrical contact with identical solutions.

Another alternative is that disclosed by Hjertén, U.S. Pat. No. 4,911,808, issued Mar. 27, 1990. Mobilization according to this patent is achieved by the addition of cations other than protons (such as $Na^+$, for example) to the anolyte, or anions other than hydroxyl groups (such as $Cl^-$, for example) to the catholyte. When voltage is applied, migration of these ions into the capillary causes a change in the concentration of the proton or hydroxyl ion, respectively, in the separation medium. The resultant shift in pH imparts charge to the focused proteins and ampholytes, which now migrate in the appropriate direction and are thus mobilized.

These latter two methods are effective for many systems. In some systems, however, these methods do not produce mobilization with equal effectiveness for all peaks. In some cases, for example, late-migrating or slow-moving peaks are broadened during the mobilization, and may not appear at the detection point at all.

SUMMARY OF THE INVENTION

These and other inadequacies of mobilization systems are addressed by the present invention. In accordance with this invention, protein zones and ampholyte zones in general which have been isoelectrically focused are mobilized by introducing into either the anolyte or catholyte or both a further ampholyte having an isoelectric point which falls between the pH's of the anolyte and catholyte, then applying a voltage between the anolyte and catholyte to cause migration of the added ampholyte toward its equilibrium position into the focusing medium in the same manner as the ampholytes previously focused. The volume of the added ampholyte is large, however, compared to the volume of the focusing medium, and the voltage is maintained to achieve a continuous migration of the added ampholyte from the anolyte or catholyte chamber into the focusing medium. The added ampholyte thus forms a continuously expanding zone in the medium, gradually filling the medium and displacing the previously focused zones either past a detection point or out of the medium.

The invention extends to a wide range of embodiments, the features and advantages of which will be apparent from the description which follows.

DETAILED DESCRIPTION OF THE INVENTION AND PREFERRED EMBODIMENTS

Figure 1:
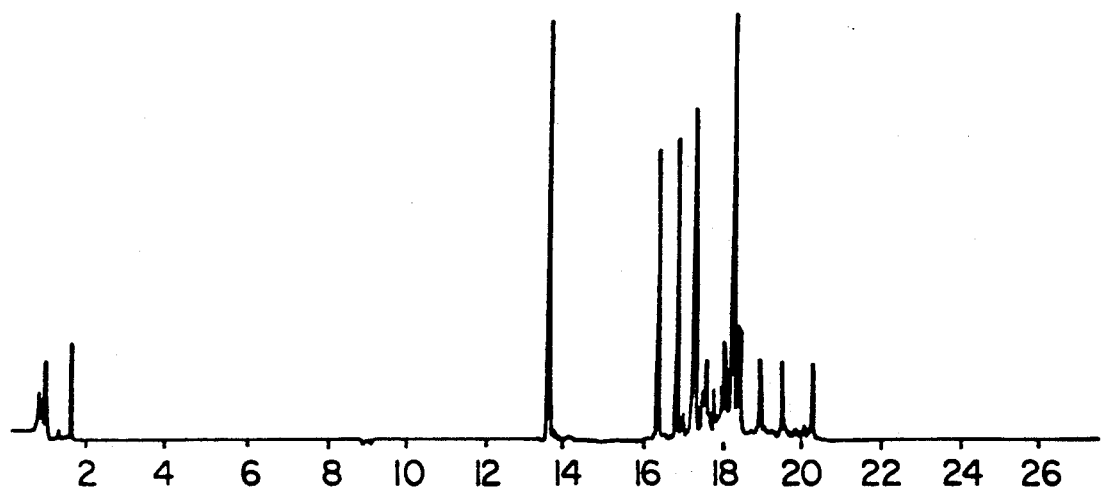
FIG. 1 is an illustration of a mobilization method outside the scope of this invention, included for purposes of comparison. The figure shows a recorder strip chart trace of a detector output showing, absorbance due to mobilized isoelectrically focused zones.

Ampholytes used for displacement of the focused zones in the present invention will be selected on the basis of their isoelectric points. These ampholytes may also be termed zwitterions, or alternatively described as being in a zwitterion state at their isoelectric points. These ampholytes are designated herein by the terms "mobilization ampholyte" and "zwitterion," which are used herein interchangeably to distinguish these ampholytes from the ampholytic species which were separated into zones in the focusing stage, and from the carrier ampholyte which is a mixture of species having a pH range and which is commonly included as part of the focusing medium for the purpose of forming a pH gradient. Examples of carrier ampholytes are Bio-Lyte ® ampholytes, a series of carrier ampholytes characterized by different pH ranges, available from Bio-Rad Laboratories, Inc., Hercules, California, and Pharmalyte ampholytes, a similar series available from Pharmacia Fine Chemicals, Uppsala, Sweden.

Suitable zwitterions are those which have well-defined isoelectric points which lie between the pH values of the anolyte and catholyte used in a typical isoelectric focusing procedure. The pH range defined by the gradient in the focusing medium established by the anolyte and catholyte and the carrier ampholyte will thus encompass the isoelectric point of the zwitterion, and the equilibrium or zwitterion state of the zwitterion, i.e., the state at which the zwitterion is no longer mobile under the influence of the electric field, will accordingly be attained at a point in the focusing medium rather than in either the catholyte or anolyte.

To achieve displacement of the previously focused zones either past a detection point or out of the medium, the quantity of zwitterion which is introduced into the chosen electrolyte and permitted to migrate under the influence of the applied voltage will be large relative to the total amounts of solutes in the focused zones, and large relative as well to the separation medium volume. This will result in an expanding zwitterion zone which continues to expand until it occupies a majority if not all of the volume of the separation medium.

In the preferred practice of the invention, the separation medium is a capillary with an internal volume which is at least two or three orders of magnitude smaller than the volume of either or both of the two electrode chambers. In such systems, addition of the zwitterion to the selected electrode chamber at even very low concentrations will provide ample zwitterion sufficient to displace the entire focused zone pattern. For example, when using a capillary with internal diameter on the order of 100 microns and length on the order of 25 cm, and electrode chambers with volumetric capacities on the order of 100 $\mu$L, a zwitterion concentration in one electrode chamber of as low as 1 mM will produce the desired zone mobilization. In general, the actual quantity or concentration of zwitterion is not critical and may vary widely. Smaller concentrations tend to result in slower mobilization velocities than larger amounts. Preferred concentrations range from about 10 mM to about 1.0 M, and most preferred are from about 30 mM to about 300 mM. The optimum in any particular system will depend on the dimensions and volumes of the system components, and will be either readily apparent to the skilled laboratory technician or readily determinable by routine experimentation.

Selection of a zwitterion according to the value of its isoelectric point is a means of controlling the direction of mobilization. The selection will be made in relation to the range of isoelectric points of the focused zones. For example, a zwitterion having an isoelectric point which is lower than those of the focused zones will cause the zwitterion to initially migrate to a point along the focusing path between the focused zone pattern and the anolyte. As further zwitterion migrates toward that point, an expanding zone of zwitterion will form around (i.e., grow in either direction from) that point, modifying and shifting the pH gradient and displacing the focused zones toward the catholyte. A zwitterion having an isoelectric point which is higher than those of the focused zones will form a zone expanding from a point between the focused zone pattern and the catholyte, causing displacement of the focused zone pattern toward the anolyte. A zwitterion having an isoelectric point which is within the range defined by the focused zones will form a zone expanding in both directions from a point within the zone pattern, causing focused zones on the anolyte side of the expanding zone to be displaced toward the anolyte at the same time that zones on the catholyte side are being displaced toward the catholyte.

For purposes of mobilizing focused zones in general, all such mobilization patterns have utility and are within the scope of the invention. Thus, for single direction mobilizations in capillary systems, detection may be performed at one point along the direction of mobilization, and solute recovery if desired may be achieved at one end of the capillary, whereas for dual direction mobilizations, detection may be performed simultaneously at two points located near opposite ends of the capillary and solutes recovered from both ends of the capillary. By appropriate selection of the zwitterion, one may selectively detect focused solutes with isoelectric points within specified ranges, i.e., either above or below a specified value. In most cases, mobilization in a single direction for all focused solute zones will be the most useful application of the invention, and accordingly the zwitterion will be one which has an isoelectric point either greater than or less than the entire array of isoelectric points of the focused zones.

The zwitterion may be placed in either of the two electrode chambers, and the choice can be made independently of the location along the focusing path from which the expanding zwitterion zone will originate and thus independently of the direction in which the focused zones will travel during mobilization. In preferred embodiments of the invention, however, the source chamber will be the chamber furthest away from the point where the expanding zone will originate and toward which the focused zones will be travel as they are mobilized by the expanding zone. Thus, for zwitterions migrating to positions along the capillary between the focused zones and the anolyte, the source chamber is preferably the catholyte chamber, and for zwitterions migrating to positions between the focused zones and the catholyte, the source chamber is preferably the anolyte chamber.

With these considerations in mind, the isoelectric point of the zwitterion is not critical and may vary widely. In most systems where unidirectional zone mobilization is sought, and where the anolyte has a pH of about 2 or below and the catholyte has a pH of about 12 or above, best results will be obtained with a zwitterion having an isoelectric point within the range of about 2.1 to about 4.0 or within the range of about 9.0 to about 11.9, depending on the desired direction of mobilization. Thus, when mobilization toward the catholyte is sought, the zwitterion is preferably one with an isoelectric point of about 2.1 to about 4.0 and is placed in the catholyte. Likewise, when mobilization to the anolyte is sought, the zwitterion is preferably one with an isoelectric point of about 9.0 to about 11.9 and is placed in the anolyte.

A wide variety of chemical compounds may be used as mobilization ampholytes or zwitterions in the practice of the present invention. It is preferred that the zwitterion be of low molecular weight in comparison to the solutes in the focused zones so that the zwitterion migrates freely from the source chamber though the focused zones to the expanding zone causing a minimum of interference with the focused zones and thus without causing a loss in zone resolution. Particularly useful zwitterions are amino acids, including both the common naturally occurring amino acids and derivatives and analogs thereof, as well as additional amino acids which do not occur in nature. For mobilization toward the catholyte, for example, acidic amino acids such as glutamic acid (pI=3.22) and aspartic acid (pI=2.76) may be used. For mobilization toward the anolyte, basic amino acids such as arginine (pI=10.76) and lysine (pI=9.74) may be used. For mobilization in both directions, neutral amino acids such as $\beta$-alanine (pI=6.9), glycine (pI=5.97), histidine (pI=7.59), leucine (pI=5.98), and isoleucine (pI=6.02) may be used. The choice of optical isomer will not affect the utility of these amino acids.

The mobilization solution, i.e., the solution of the zwitterion which occupies the selected electrode chamber during the mobilization stage, may be prepared in a variety of ways. For zwitterions with high or low isoelectric points, it is preferable to prepare the mobilization solutions by titrating the anolyte acid or the catholyte base with the zwitterion to a fixed pH which is either acidic or basic, respectively. For zwitterions with isoelectric points close to neutrality, mobilization with a neat aqueous solution of the zwitterion has been found most effective.

The present invention extends to a wide array of isoelectric focusing systems and media. Mobilization according to the present invention may be achieved in liquid media, gel media and suspensions. Aqueous liquid media and aqueous gels are generally preferred. Mobilization is readily achieved immediately following the focusing stage with no change in the focusing medium. The medium may therefore contain any of the additives normally included for isoelectric focusing. These include carrier ampholytes as mentioned above, additives to suppress protein precipitation, and other materials as well known among those skilled in the art.

The separation medium may assume any physical configuration which will permit the resolution of solutes into zones along a single longitudinal axis. Preferred configurations will be those which promote the rapid dissipation of heat generated by the electrical current, so as to minimize the distortion of the zones during both focusing and mobilization. Thin-walled, small diameter capillary tubes are preferred, particularly when on-line detection is used. This invention is particularly useful in capillaries with internal diameters of 500 microns or less, and more particularly with those of 100 microns or less. Systems which also include means to suppress electroendosmosis are also preferred. This may be achieved by coatings on the inner capillary wall to render the wall electrically neutral and eliminate or substantially reduce any zeta potential. Examples of such coatings are methyl cellulose and non-crosslinked polyacrylamide. Coatings such as these offer the further advantage of suppressing solute adsorption at the wall surface. Such coatings and additional methods of electroendosmosis suppression are known among those skilled in the art.

The isoelectric focusing which precedes the mobilization is done according to conventional methods. A pH gradient is established by carrier ampholytes between the anolyte and catholyte. A voltage is then applied until steady state, i.e., one in which the solutes are isolated into focused zones and are no longer migrating, is achieved.

In the mobilization stage once the zwitterion has been added to the system, the applied voltage will be in the same polarity as the voltage in the focusing stage, and generally at about the same or a higher level. The voltage may be adjusted during the mobilization so that the zones travel with a minimum of distortion and at a substantially steady linear velocity. This is optional, however, and in many cases the most important consideration will be the use of a standard operating procedure consistently used from one run to the next to achieve reproducibility and the ability to make direct comparisons among runs.

The following examples are offered for illustrative purposes only. They are intended neither to limit nor to define the invention in any manner.

EXAMPLE

This example illustrates mobilization of isoelectrically focused zones of a protein mixture, utilizing a mobilization technique in accordance with the present invention, and comparing the results with results obtained using a mobilization technique in accordance with Hjertén, U.S. Pat. No. 4,911,808.

In each of the two experiments, isoelectric focusing was performed in a fused silica capillary whose interior surface was coated with linear polyacrylamide as described by Hjertén, U.S. Patent No. 4,680,201, issued Jul. 14, 1987. The capillary was 14 cm in length by 25 $\mu$ internal diameter; the sample was run in 2% Bio-Lyte® 3/10 (an ampholyte commercially available from Bio-Red Laboratories, Inc., Hercules, California, U.S.A.); the anolyte was 10 mM phosphoric acid at pH 2.3, and the catholyte was 20 mM NaOH at pH 12; and the voltage during focusing was 8 kV. The anolyte and catholyte chambers in these experiments had volumetric capacities of approximately 100 $\mu$L and 500 $\mu$L, respectively, and were used full.

The sample being separated in each case was a Bio-Rad IEF Standard, consisting of the following proteins:

| Protein | pI |
|---|---|
| phycocyanin | 4.65 |
| $\beta$-lactoglobulin B | 5.10 |
| bovine carbonic anhydrase | 6.00 |
| human carbonic anhydrase | 6.50 |
| equine myoglobin | 7.00 |
| human hemoglobin A | 7.10 |
| human hemoglobin C | 7.50 |
| lentil lectin (three bands) | 8.20, 8.40, 8.60 |

| Protein | pI |
| --- | --- |
| cytochrome C | 9.60 |

Once isoelectric focusing was achieved, mobilization of the focused zones in one of the experiments was achieved by the addition of 80 mM sodium chloride to the catholyte, according to the reference procedure, resulting in mobilization toward the catholyte. Mobilization in the other experiment was achieved by replacing the catholyte with a basic glutamic acid solution according to the present invention, the glutamic acid solution prepared by adding sufficient glutamic acid to 0.1 N NaOH to adjust the pH to 10.5. This resulted in a 50 mM glutamic acid solution (0.74% by weight). In both experiments, a voltage of 8 kV was then applied and mobilization proceeded.

Figure 2:
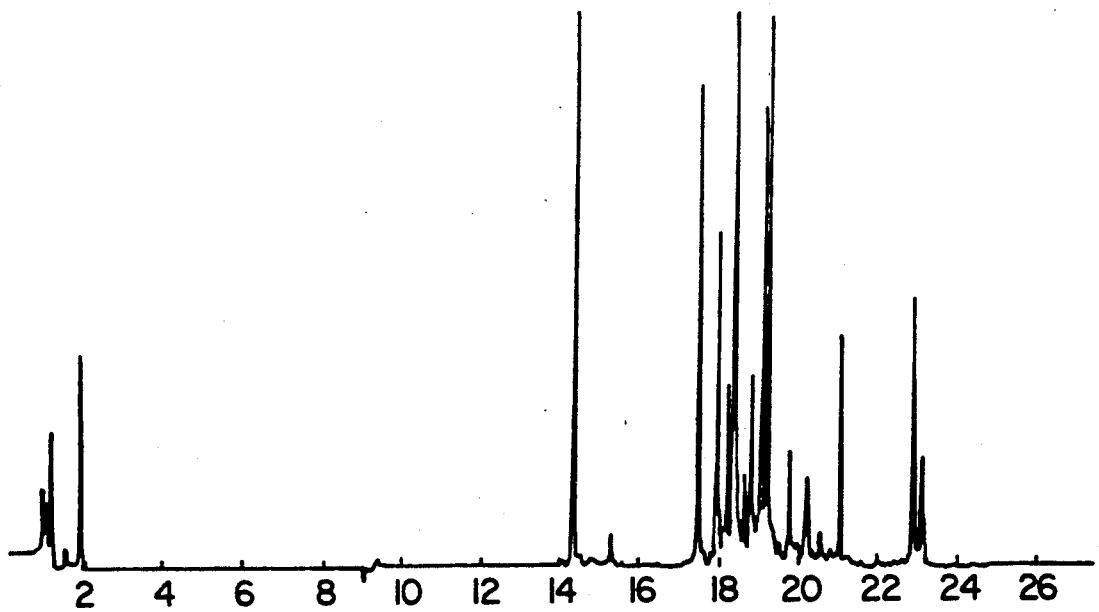
FIG. 2 is a recorder strip chart trace taken using a mobilization technique in accordance with the invention, all other system parameters being identical to those of FIG. 1.

The results are shown in FIGS. 1 and 2, which are strip chart recorder traces from an absorbance detector at 280 nm. A comparison of the traces indicates that the glutamic acid method of the present invention enables mobilization of proteins at extremes of pI, i.e., very acidic or very basic. Thus, phycocyanin is seen to migrate at 23 min with glutamic acid mobilization, but does not appear with salt mobilization.

The foregoing is offered primarily for purposes of illustration. It will be readily apparent to those skilled in the art that the methods, materials and system parameters may be further varied beyond what is described herein without departing from the spirit and scope of the invention.

What is claimed is:

1. A method for the mobilization of zones of ampholyte substances isoelectrically focused in an ampholytic separation medium between an anolyte at a first pH and a catholyte at a second pH higher than said first pH, said method comprising:
   (a) introducing into either said anolyte or said catholyte an ampholyte having an isoelectric point between said first and second pH's and defined as a mobilization ampholyte; and
   (b) applying a voltage between said anolyte and said catholyte to cause migration of said mobilization ampholyte into said ampholytic separation medium, and maintaining said voltage to form a continuously expanding zone of said mobilization ampholyte in said ampholytic separation medium, thereby displacing each of said isoelectrically focused zones by said expanding zone past a locus of detection.

2. A method in accordance with claim 1 in which the isoelectric points of said ampholyte substances of said isoelectrically focused zones define a range of values, and the isoelectric point of said mobilization ampholyte is outside of said range of values.

3. A method in accordance with claim 2 in which the isoelectric point of said mobilization ampholyte is below said range.

4. A method in accordance with claim 2 in which the isoelectric point of said mobilization ampholyte is about 4.0 or less, and step (a) comprises introducing said mobilization ampholyte into said catholyte.

5. A method in accordance with claim 2 in which the pH of said anolyte is about 2 or below, the pH of said catholyte is about 12 or above, the isoelectric point of said mobilization ampholyte is from about 2.1 to about 4.0, and step (a) comprises introducing said mobilization ampholyte into said catholyte.

6. A method in accordance with claim 2 in which the isoelectric point of said mobilization ampholyte is above said range.

7. A method in accordance with claim 2 in which the isoelectric point of said mobilization ampholyte is about 9.0 or higher, and step (a) comprises introducing said mobilization ampholyte into said anolyte.

8. A method in accordance with claim 2 in which the pH of said anolyte is about 3 or below, the pH of said catholyte is about 12 or above, the isoelectric point of said mobilization ampholyte is from about 9.0 to about 11.9, and step (a) comprises introducing said mobilization ampholyte into said anolyte.

9. A method in accordance with claim 1 in which said mobilization ampholyte is an amino acid.

10. A method in accordance with claim 1 in which said ampholytic separation medium is a liquid solution in a capillary having an internal diameter of 500 microns or less.

11. A method in accordance with claim 1 in which said ampholytic separation medium is a liquid solution in a capillary having an internal diameter of 100 microns or less.

* * * * *